US008609382B1

(12) United States Patent
Hughes et al.

(10) Patent No.: US 8,609,382 B1
(45) Date of Patent: Dec. 17, 2013

(54) SCHEFFERSOMYCES STIPITIS STRAIN FOR INCREASED ETHANOL PRODUCTION AND USES THEREOF

(75) Inventors: Stephen R. Hughes, Peoria, IL (US); William R. Gibbons, Brookings, SD (US)

(73) Assignee: The United States of America, as represented by the Secretary of Agriculture, Washington, DC (US)

( * ) Notice: Subject to any disclaimer, the term of this patent is extended or adjusted under 35 U.S.C. 154(b) by 0 days.

(21) Appl. No.: 13/564,110

(22) Filed: Aug. 1, 2012

Related U.S. Application Data

(60) Provisional application No. 61/514,518, filed on Aug. 3, 2011.

(51) Int. Cl.
| | |
|---|---|
| *C12P 7/06* | (2006.01) |
| *C12P 7/04* | (2006.01) |
| *C12P 7/02* | (2006.01) |
| *C12P 7/00* | (2006.01) |
| *C12P 1/02* | (2006.01) |
| *C12N 1/00* | (2006.01) |
| *C12P 7/08* | (2006.01) |
| *C12P 7/10* | (2006.01) |
| *C12N 1/16* | (2006.01) |
| *C12N 15/01* | (2006.01) |
| *C12N 15/00* | (2006.01) |
| *C12N 13/00* | (2006.01) |

(52) U.S. Cl.
USPC ........... 435/161; 435/157; 435/155; 435/132; 435/41; 435/171; 435/448; 435/446; 435/440; 435/255.5; 435/255.1; 435/243; 435/254.1; 435/163; 435/165

(58) Field of Classification Search
None
See application file for complete search history.

(56) References Cited

U.S. PATENT DOCUMENTS

2012/0184020 A1* 7/2012 Picataggio et al. ...... 435/254.21

OTHER PUBLICATIONS

Hughes et al.,Random UV-C mutagenesis of Scheffersomyces (formerly Pichia) stipitis NRRL Y-7124 to improve anaerobic growth on lignocellulosic sugars, J. Ind. Microbiol. Biotech., Jul. 2011, 39, 163-73.*
Bahareh et al., Increasing the bioethanol yield in the presence of furfural via mutation of a native strain of *Saccharomyces cerevisiae*, African J. Microbiol. Res., Mar. 2011, 5, 651-56.*
Hashimoto et al., Isolation of auxotrophic mutants of diploid industrial yeast strains after UV mutagenesis, Appl. Environ. Microbiol., 2005, 312-19.*

* cited by examiner

*Primary Examiner* — Rebecca Prouty
*Assistant Examiner* — Todd M Epstein
(74) *Attorney, Agent, or Firm* — John Fado; Albert Y. Tsui; Lesley Shaw

(57) ABSTRACT

Described are novel *S. stipitis* strains that were obtained by UV-C irradiation of wild-type *S. stipitis* NRRL Y-7124 cultures, followed by 5-month anaerobic growth on xylose at 28° C. The UV-C-mutagenized strains were able to grow anaerobically on xylose or glucose medium with higher ethanol production than a *Saccharomyces cerevisiae* yeast strain under comparable fermentation conditions. The mutagenized strains were identified by DNA fingerprinting to be unique strains closely related to wild-type *Scheffersomyces stipitis*. These mutagenized strains have potential application in large-scale industrial conversion of lignocellulosic sugars to fuel ethanol.

6 Claims, 10 Drawing Sheets

US 8,609,382 B1

SCHEFFERSOMYCES STIPITIS STRAIN FOR INCREASED ETHANOL PRODUCTION AND USES THEREOF

CROSS-REFERENCE TO RELATED APPLICATION

This present application claims priority under 35 U.S.C. §119(e) to U.S. Provisional Ser. No. 61/514,518, which was filed on Aug. 3, 2011, and is hereby incorporated by reference.

FIELD OF INVENTION

The present invention is for novel *Scheffersomyces stipitis* yeast strains that produce ethanol. More specifically, the mutagenized yeast strains are able to ferment hexose sugars and pentose sugars to yield ethanol.

BACKGROUND OF INVENTION

Over 90% of ethanol biofuel produced in the United States is made from corn starch using *Saccharomyces* strains to ferment the glucose obtained by hydrolysis of the starch. The United States Environmental Protection Agency has revised the Renewable Fuel Standard (RFS) program as required by the Energy Independence and Security Act of 2007 (EISA). The final rule (RFS2) increases the volume requirements for total renewable fuel to 20.5 billion gallons and for cellulosic biofuel to 3.0 billion gallons by 2015. To meet these mandates, it will be necessary to use cellulosic biomass, an abundant and renewable carbon source, as a feedstock. However, the microbial strains used to ferment the glucose released by hydrolysis of starch are not capable of fermenting the more diverse mixture of sugars released by hydrolysis of lignocellulosic biomass. *Saccharomyces* strains are generally capable of fermenting the hexose sugars, glucose and galactose; however, they do not naturally ferment the pentose sugars, xylose or arabinose.

To efficiently convert lignocellulo sic biomass to ethanol, it will be necessary to produce a yeast strain capable of utilizing both pentoses and hexoses. The well-studied yeast *Scheffersomyces* (formerly *Pichia*) *stipitis* has the potential to be used more effectively for biomass conversion into ethanol than *Saccharomyces* strains because it can naturally ferment both pentose and hexose sugars. The strain produces up to 47 g/L ethanol on xylose under conditions of limited aeration and gives ethanol yields up to 0.41 gram/gram on wheat straw hydrolysate. However, *S. stipitis* has a slower sugar consumption rate than *Saccharomyces* and requires oxygen for both growth and maximal ethanol production.

Because microaerophilic conditions are difficult to maintain uniformly in large-scale industrial fuel ethanol operations, enhancing the capability of this yeast to produce ethanol anaerobically could increase its value in industrial processes. As such, there is a need develop *Scheffersomyces stipitis* yeast strains that produce ethanol that can ferment hexose sugars and pentose sugars in large-scale industrial fuel ethanol operating conditions.

BRIEF DESCRIPTION OF THE DRAWINGS

The present invention together with the above and other objects and advantages may best be understood from the following detailed description of the embodiment of the invention illustrated in the drawings, wherein.

Deposit of Biological Material

Figure 1A:
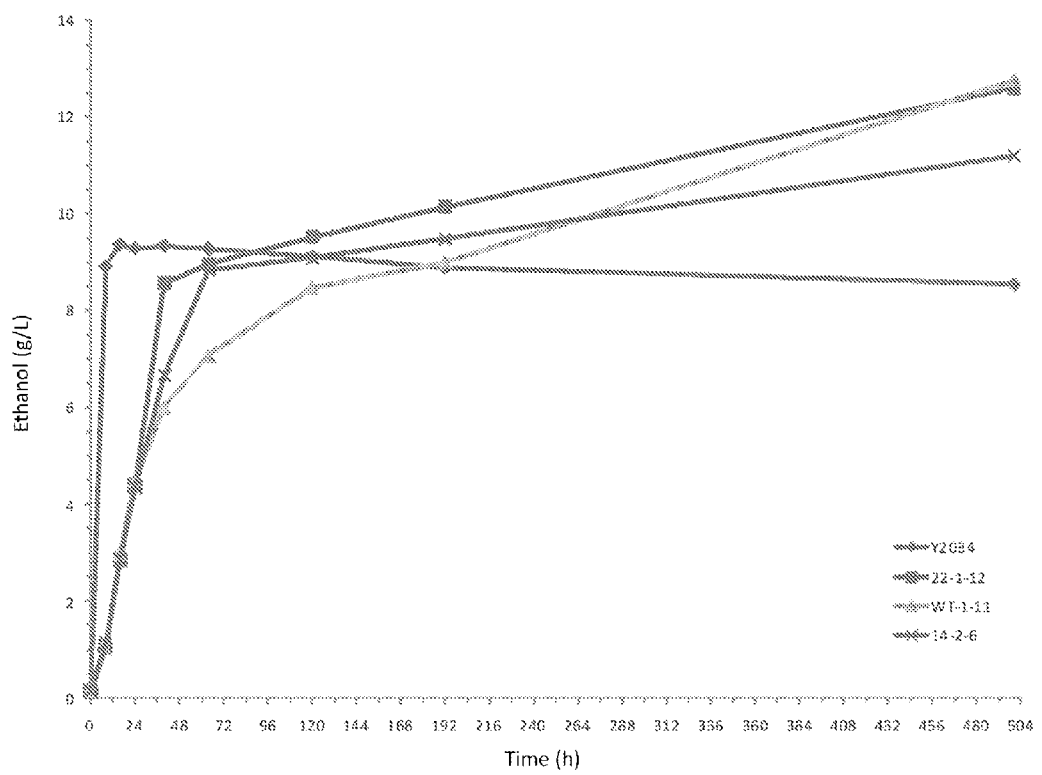
FIG. 1A is a graph depicting ethanol production by mutagenized strains in liquid culture containing xylose plus glucose compared to wild-type (WT) strain, *Saccharomyces cerevisiae* NRRL Y-2034 at anaerobic conditions (nitrogen in headspace) with a DASGIP reactor.

Strains Y-50472 and Y-50473 are identified as variants of *Scheffersomyces stipitis* based on variable nucleotide tandem repeat (VNTR) analysis. Both NRRL Y-50472 and NRRL Y-50473 were deposited on Mar. 2, 2011, under the provisions of the Budapest Treaty in the Agricultural Research Culture Collection (NRRL) in Peoria, Ill., and have been assigned Accession Nos. NRRL Y-50472 and NRRL Y-50473.

Strain Y-22-1-1 was identified as variants of *Scheffersomyces stipitis* based on variable nucleotide tandem repeat (VNTR) analysis.

The subject cultures have been deposited under conditions that assure that access to the cultures will be available during the pendency of this patent application to one determined by the Commissioner of Patents and Trademarks to be entitled thereto under 37 CFR §1.14 and 35 USC §122. The deposits are available as required by foreign patent laws in countries wherein counterparts of the subject application, or its progeny, are filed. However, it should be understood that the availability of the deposits does not constitute a license to practice the subject invention in derogation of patent rights granted by governmental action.

Further, the subject culture deposits will be stored and made available to the public in accord with the provisions of the Budapest Treaty for the Deposit of Microorganisms, i.e., they will be stored with all the care necessary to keep them viable and uncontaminated for a period of at least five years after the most recent request for the furnishing of a sample of the deposits, and in any case, for a period of at least 30 (thirty) years after the date of deposit or for the enforceable life of any patent which may issue disclosing the cultures. The depositor acknowledges the duty to replace the deposits should the depository be unable to furnish a sample when requested, due to the condition of the deposits. All restrictions on the availability to the public of the subject culture deposits will be irrevocably removed upon the granting of a patent disclosing them.

As described herein, *Scheffersomyces stipitis* strain NRRL Y-50472 is also referred to as strain 14-2-6. *Scheffersomyces stipitis* strain NRRL Y-50473 is also referred to as strain 22-1-12. As used herein, the binomial name *Scheffsomyces stipitis* and the former name *Pichia stipitis* refer to the same yeast species.

DETAILED DESCRIPTION OF THE INVENTION

Disclosed herein is an isolated *Scheffersomyces stipitis* having been deposited with the United States Department of Agriculture, Agricultural Research Patent Culture Collection as Accession Deposit Number NRRL Y-50472. Also disclosed is an isolated *Scheffersomyces stipitis* having been deposited with the United States Department of Agriculture, Agricultural Research Patent Culture Collection as Accession Deposit Number NRRL Y-50473.

Disclosed herein is a method of producing ethanol comprising culturing yeast strain NRRL Y-50472 or NRRL Y-50473 under suitable conditions for a period of time sufficient to allow fermentation of at least a portion of feedstock to ethanol. In one embodiment of the invention, the method includes culturing yeast strains NRRL Y-50472 or NRRL Y-50473 anaerobically with cellobiose and glucose. In yet another embodiment of the invention, the yeast strains NRRL Y-50472 or NRRL Y-50473 ferment cellobiose at microaerophilic conditions, an aerobic conditions, and aerobic conditions. In another embodiment of the invention, the yeast strains ferment a combination of xylose, cellobiose, and glucose under aerobic conditions.

Strain Construction

Preparation of Isolates 14 and 22

Duplicate 2-L Fernbach flasks were prepared by adding 1 L of YM medium [0.3% Yeast Extract and 0.3% Malt Extract, 0.5% Peptone (Becton Dickinson, Sparks, Md., USA), 0.1% Dextrose (Sigma, St. Louis, Mo., USA)] to each flask and inoculating with 20 mL of a 2-day YM 28° C. culture of wild-type *S. stipitis* NRRL Y-7124 (USDA, ARS Culture Collection) from a 100-mL flask. The Fernbach flasks were incubated at 28° C. for 2 days with shaking at 100 rpm. Before irradiation, a sample of the log phase culture was taken from the Fernbach flask to obtain an estimate of the number of cells using a Reichert Neubauer/Bright-Line® Hemacytometer (American Optical Corp., Buffalo, N.Y., USA). The culture from each flask was divided into two Beckman 500-mL spin bottles and centrifuged in a Beckman Avanti J20 centrifuge (Beckman; Indianapolis, Ind., USA) at 20° C. for 20 minutes at 3000 rpm. Cell pellets were washed with sterile water, and each pellet was resuspended in 50 mL of sterile water. A 25-mL aliquot was taken from each resuspension and placed into a Marsh RR-0014 deep trough plate with baffled bottom (Marsh Biomedical Products, Inc.; Rochester, N.Y., USA). The plates were placed 14 cm below a source of UV-C radiation (234 nm; UVP, LLC Light Table (inverted); Upland, Calif., USA) and irradiated for 1 minute.

From each trough plate, using an automated protocol on the robotic workcell, 600-µL aliquots were spread onto 128×96 mm Omni Tray plates (Thermo Fisher Scientific, Waltham Mass., USA) containing 2% xylose complete minimal medium plus all amino acids, consisting of 1.4 g yeast synthetic drop-out medium supplement (minus histidine, leucine, tryptophan, and uracil); 0.06 g L-leucine; 0.04 g L-tryptophan; 0.02 g L-histidine; 0.02 g uracil; 20 g D-xylose (Sigma Aldrich, St. Louis, Mo., USA); 15 g Bacto™ Agar (Thermo Fisher Scientific, Waltham, Mass., USA); 6.7 g yeast nitrogen base without amino acids (inositol, $CaCl_2$, NaCl, $MgSO_4$, $(NH_4)_2SO_4$, and $KH_2PO_4$; Sigma Aldrich, St. Louis, Mo., USA); and 5 g ammonium sulfate per liter. The spread plates (96 plates per Fernbach flask, therefore a total of 192 plates prepared from the 1-minute irradiation) were bundled into sets of 6, wrapped in saran wrap, sealed with parafilm, and placed into a Mitsubishi anaerobic chamber (Mitsubishi Gas Chemical America, Inc., New York, N.Y., USA) containing the AnaeroPack dry chemical system (Sigma Fluka, Buchs, Switzerland) at 28° C. for 5 months to select for strains that could survive anaerobically for an extended period of time unlike the wild-type strain.

Two colonies, designated 14 and 22, were found still growing in mounds above the background when the bundled spread plates were unwrapped after this lengthy anaerobic incubation on xylose medium. Duplicate samples were picked from these colonies and spread onto plates containing rich YM or YPD [1.0% Yeast Extract, 2.0% Bacto Peptone, 2.0% D-glucose, and 20 g/L BactoAgar (Thermo Fisher Scientific, Waltham, Mass., USA)] or 2% xylose complete minimal medium plus all amino acids and incubated at 28° C. for 2 weeks anaerobically to check that these isolates were still capable of growth on glucose and to eliminate background. Five surviving colonies were picked from the re-spread anaerobic xylose plates onto plates containing YM, YPD, or xylose complete minimal medium plus all amino acids and incubated aerobically at 28° C. for 3 days to verify this growth capability was still present and to provide starter cultures for the second round of irradiation. Two 100-mL flasks were inoculated with samples from isolates 14 and 22 from the YM plates and incubated at 28° C. for 3 days to prepare samples for inoculation into Fernbach flasks for more intensive irradiation. Glycerol (18% v/v) stocks of isolates 14 and 22 were also prepared.

Strains with Improved Anaerobic Growth on Xylose from 1-Minute UV-C Irradiation (Isolates 14 and 22)

Figure 4A:
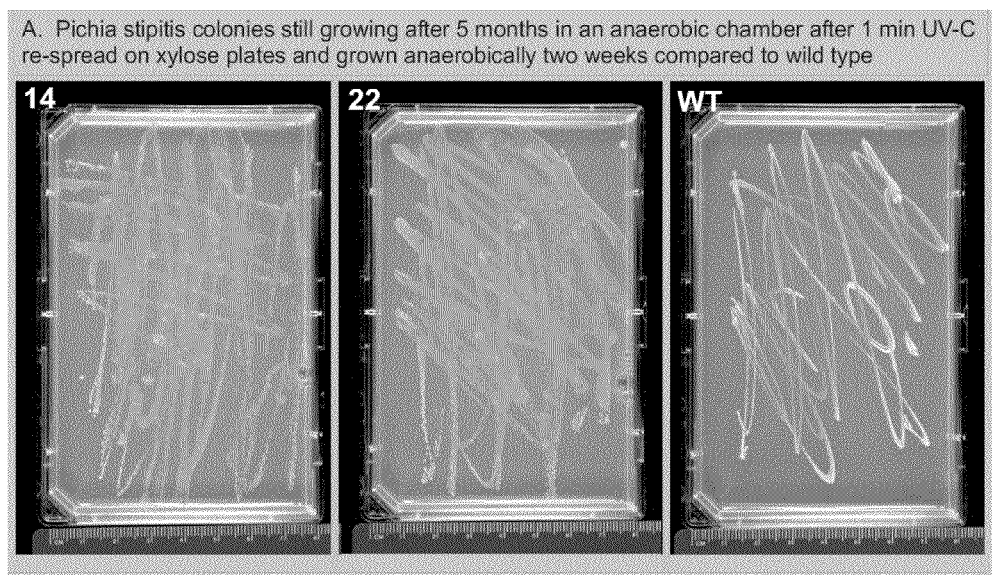
FIG. 4A is a photo of *Scheffersomyces stipitis* colonies (designated 14 and 22) that were still growing above background on xylose complete minimal medium plus all amino acids with nitrogen base after 1-minute irradiation with UV-C and 5-month anaerobic incubation and that were re-spread on the same medium and incubated anaerobically for 2 weeks to isolate the colonies.
Figure 4B:
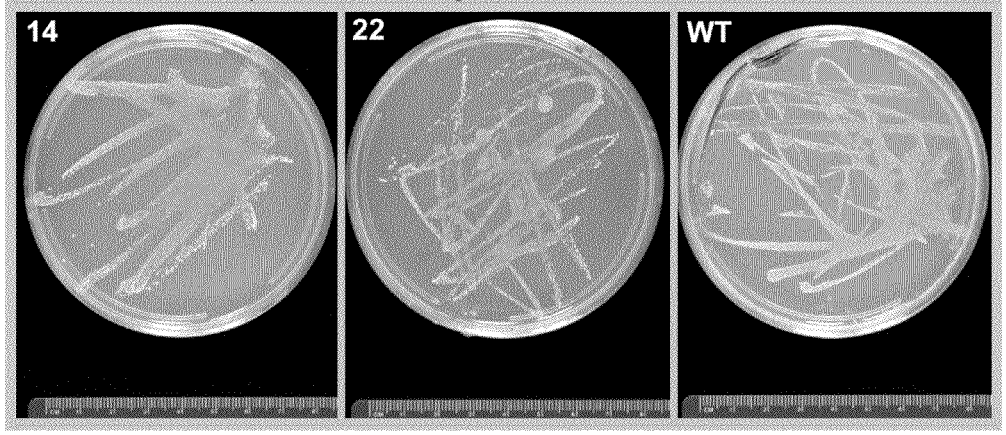
FIG. 4B is a photo of *Scheffersomyces stipitis* colonies from the 2-week anaerobic xylose plates that were recovered on the same medium and grown aerobically to confirm capability for aerobic growth was maintained.
Figure 4C:
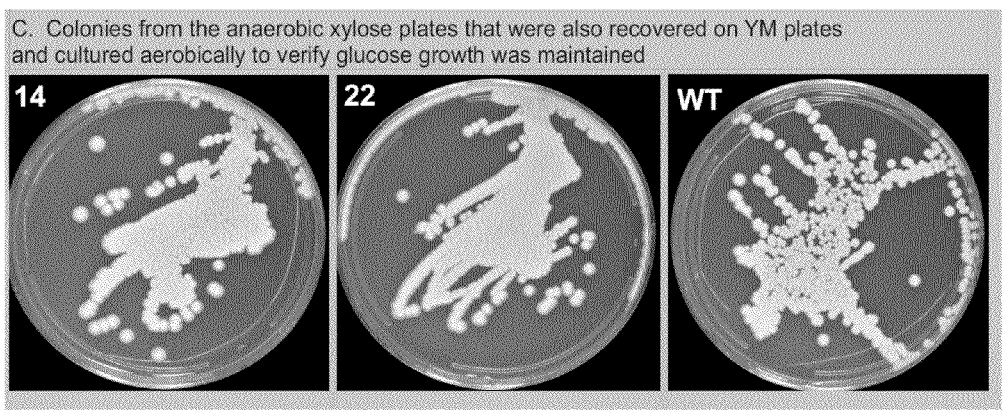
FIG. 4C is a photo of *Scheffersomyces stipitis* colonies from the 2-week anaerobic xylose plates that were also recovered on YM medium and cultured aerobically to confirm ability to utilize glucose was maintained.

When the wild-type strain was subjected to 234 nm UV-C irradiation for 1 minute and incubated in an anaerobic chamber for 5 months on 2% xylose minimal medium plus all amino acids with nitrogen base, the resulting plates showed considerable background growth, but two colonies, designated 14 and 22, appeared as mounds above the background lawn. These colonies were re-spread on the same medium and grown anaerobically for 2 weeks to isolate single colonies (FIG. 4A). The colonies from the anaerobic xylose plates were recovered on the same medium and cultured aerobically to confirm aerobic growth was maintained by the two mutagenized strains (FIG. 4B). Because actual industrial conditions are neither fully aerobic nor fully anaerobic but rather microaerophilic, both capabilities are important for optimum performance of an industrial yeast strain. When recovered on YM plates, the mutagenized strains 14 and 22 demonstrated they had also maintained the ability to utilize glucose aerobically (FIG. 4C).

Although it had been demonstrated that mutagenized strains with improved anaerobic xylose-utilization ability could be obtained by UV-C irradiation, it was reasoned that increased mutant formation or trait generation could be obtained with a longer irradiation time and at the same time this would reduce background growth. Thus, isolates 14 and 22 and the wild-type strain were subjected to further irradiation for a longer period of time.

Preparation of Strains WT-1-11, WT-2-1, 14-2-6, 22-1-1, and 22-1-12

Eight 2-L Fernbach flasks were prepared by adding 1 L of YM medium to each flask. Four of these flasks were inoculated with wild-type S. stipitis NRRL Y-7124, two flasks were inoculated with isolate 14, and two flasks were inoculated with isolate 22, using 50-mL aliquots from the respective 100-mL flasks. Following the same procedures as described above, the Fernbach flasks were incubated, the cultures were centrifuged, and each of the cell pellets was washed and resuspended. A 25-mL aliquot was taken from each resuspension and placed into a Marsh RR-0014 deep trough plate with baffled bottom. The plates were placed 14 cm below a source of UV-C radiation and irradiated at 234 nm for 4 hours.

Before irradiation, a 10-μL sample was taken from resuspended cell pellets in the trough plate (2 trough plates per Fernbach flask), diluted $10^{-5}$, and read in the Reichert Neubauer Hemacytometer to determine the starting number of total cells. Samples were taken every hour during irradiation and plated to determine the number of surviving cells. Stirring was conducted every hour to make sure all cells were equally exposed to the radiation. The liquid depth in the trough plates was not greater than 3 mm and plates were centered under the light source.

Figure 5:
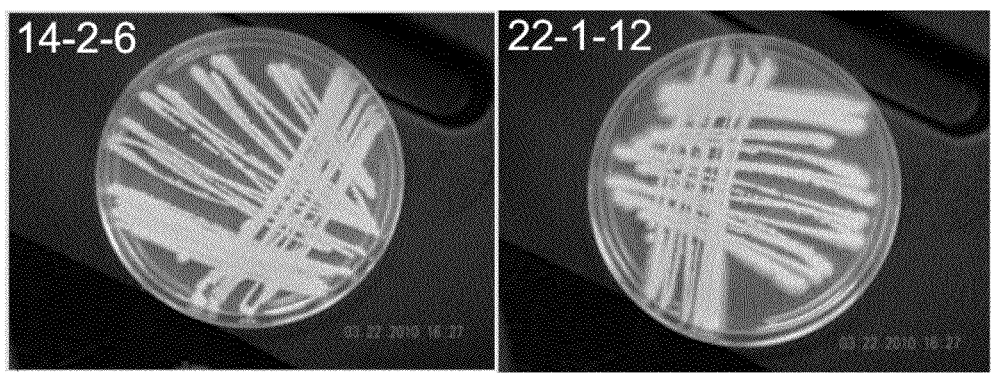
FIG. 5 is a photo of *Scheffersomyces stipitis* colonies of 14-2-6 (NRRL Y-50472) and 22-1-12 (NRRL Y-50473) after 4-hour irradiation with UV-C and 5-month anaerobic incubation grown aerobically on YPD plates for 3 days.

Spread plates (192 plates for each of the 4 strains irradiated, therefore a total of 768 plates) were prepared on the robotic workcell, moved to a HEPA-filtered hood, packaged into sets of 6, wrapped in saran wrap, sealed with parafilm, and placed into a Mitsubishi anaerobic chamber at 28° C. for 5 months. An oxygen indicator in the chamber verified absence of $O_2$. One sample from each of the 42 surviving colonies on the 768 anaerobic xylose plates was manually spread onto a plate containing rich YM, YPD, or xylose medium (one sample per plate) and incubated at 28° C. aerobically to check that these strains were still capable of growth on glucose and xylose and to obtain single isolates. After 3 days of aerobic growth on xylose, the colonies on 5 of the plates were considerably larger than those on any of the other plates, so these 5 samples, designated WT-1-11, WT-2-1, 14-2-6, 22-1-1, and 22-1-12, were selected for further characterization and evaluation. (FIG. 5 depicts colonies 14-2-6 and 22-1-12 after three days of aerobic growth.)

Growth of pseudohyphae was more pronounced on YPD medium, so colonies were spread on YPD plates, incubated aerobically at 28° C. for 3 days, and the cells examined using scanning electron microscopy.

Strains with Improved Anaerobic Growth on Xylose from 4-Hour UV-C Irradiation (Isolates 14-2-6, 22-1-1, 22-1-12, WT-1-11, and WT-2-1)

Figure 3:
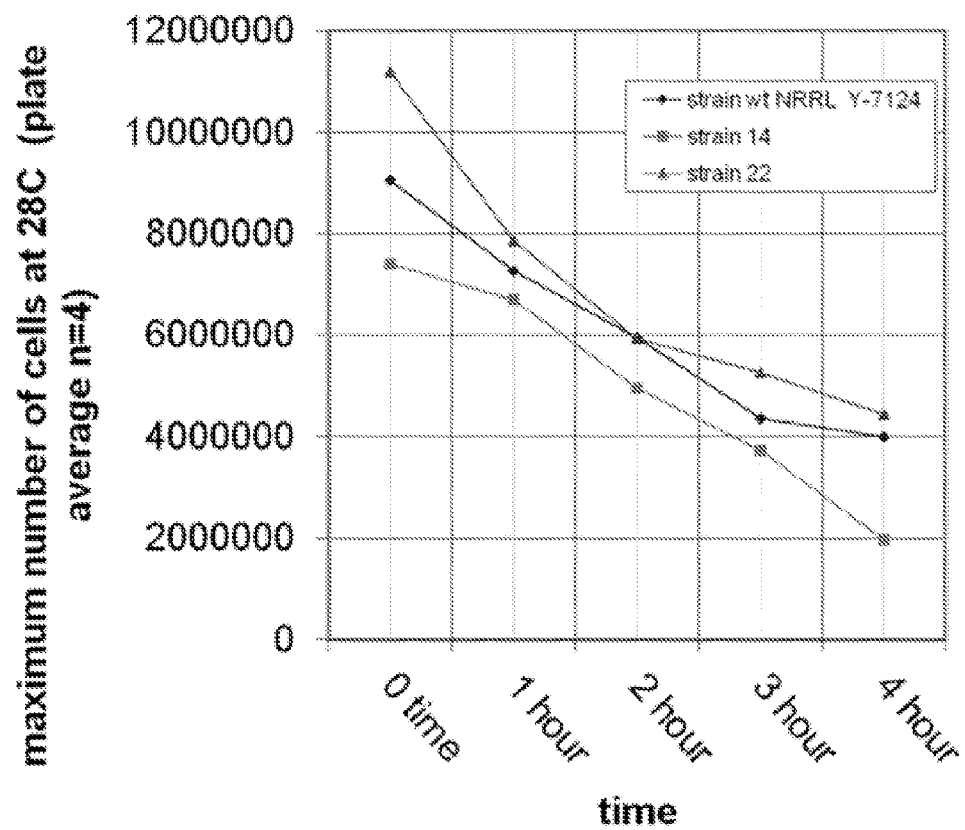
FIG. 3 is a graph depicting a kill curves of strains irradiated for four hours with UV-C 234 nm.

The progress of the second irradiation was monitored by counting the number of cells remaining at hourly intervals after initiation of irradiation of isolates 14 and 22 and the wild-type strain, with a target kill rate of about 60%. The results are presented in FIG. 3. Isolate 14 went from 7.4 million to 2.0 million cells at 4 h, for a survival rate of 27%. Isolate 22 went from 11.2 million to 4.4 million cells, a survival rate of 39%. The wild-type strain went from 9.0 million to 4.0 million cells, a survival rate of 44%. The average percentage of cells killed after 4 h was 63%. An additional advantage of the longer irradiation was that very little background growth was seen after 5 months of anaerobic growth on xylose plates so the surviving colonies were easier to isolate.

Yeast acclimation was conducted to increase ethanol yields of the strains. This was accomplished by repeated subculturing of yeast strains in a XYM broth medium containing 50 g/L xylose, 3 g/L yeast extract, 3 g/L malt extract, and 5 g/L peptone. Initially, isolated colonies were inoculated into 250 mL Erlenmeyer flasks filled with 100 mL of the XYM broth. Each flask was sealed with a rubber stopper pierced with a needle capped with a 0.2 μm filter to allow $CO_2$ venting and incubated at 35° C. and 250 rpm for 96 h, with HPLC and viable count samples taken every 24 h. At 96 h, one ml from each flask was transferred into a fresh flask of XYM broth and continually as the initial incubation. This process was repeated for 11 sequential transfers with the $12^{th}$ through $20^{th}$ transfers, the incubation period was extended to 144 hours.

Table 1 shows the actual maximum ethanol and residual xylose concentrations for acclimation trial 1 compared to the trial exhibiting the highest overall ethanol concentration. Each strain exhibited improved xylose conversion into ethanol.

TABLE 1

| Yeast Strain | Maximum Ethanol Concentration (g/L) | | Residual Xylose Conc (g/L) | |
|---|---|---|---|---|
| | Acclimation Trial 1 | Acclimation Trial with Highest Ethanol Concentration | Acclimation Trial 1 | Acclimation Trial with Lowest Xylose Concentration |
| 1-11 | 2.4 | 14.4 | 37.6 | 8.0 |
| 1-2 | 2.5 | 20.8 | 33.5 | 7.7 |
| 22-1-1 | 3.0 | 7.6 | 37.4 | 12.2 |
| 22-1-12 (NRRL Y-50473) | 1.8 | 5.8 | 40.4 | 8.7 |
| 14-2-6 (NRRL Y-50472) | 2.8 | 8.3 | 35.9 | 9.9 |

Example 2

Fermentation of Glucose, Xylose, and Cellobiose in 250-mL Erlenmeyer Flasks

The fermentation performance of the five mutagenized S. stipitis yeast strains (WT-1-11, WT-2-1, 14-2-6, 22-1-1, and 22-1-12) were evaluated for glucose, xylose, and cellobiose. Fifty g/L sugar solutions of either with glucose, xylose, and cellobiose and 5 g/L yeast extract were prepared with 100-mL quantities placed in 250-mL Erlenmeyer flasks that were closed with a rubber stopper equipped with a 21 gauge hypodermic needle and a filter for gas exchange. After autoclaving and cooling, each flask was inoculated with 1 mL of the respective S. stipitis strain (inoculum grown for 24 h at 35° C. in glucose medium). The flasks were incubated at 35° C. and 250 rpm for 96 h (aerobic) with triplicate trials. Samples were removed at 0, 3, 6, 9, 12, 24, 36, 48, 72, 96 h. Glucose, xylose, cellobiose, and ethanol were analyzed by a Waters high-performance liquid chromatography (HPLC) system with a refractive index detector, Aminex HPX-87H column (Bio-Rad, Laboratories, Inc., Hercules, Calif., USA), and mobile phase of 0.1N $H_2SO_4$ at 65° C. and 0.6 mL/min.

Ethanol Production and Substrate Use by Mutagenized Strains in 250-mL Flasks

All strains used glucose efficiently; however, strains 22-1-12 and 14-2-6 achieved the highest ethanol levels, productivities, and fermentation efficiencies, while having the lowest residual sugar levels (Table 2, top). When cellobiose was provided as the carbon source, all strains performed poorly, but in these trials strains WT-2-1 and 22-1-1 performed slightly better than the other strains (Table 2, middle). The results using xylose as the carbon source showed that the strains performing best were 14-2-6 and 22-1-12 (Table 2, bottom). However, compared to the results with glucose (about 18 g/L ethanol), these strains produced only about 3 g/L on xylose, which is about 12% of the theoretical yield (25.6 g/L for xylose). Yet the fermentation efficiency was about 30%, indicating that less than half the consumed xylose was converted to ethanol. The fermentation efficiency of the mutagenized strain on the individual sugar substrates is compared graphically in FIG. 1B. Initial concentrations of all sugar carbon sources were 50 g/L. Theoretical ethanol yield for glucose is 50 g/L [(2×46)/180]=25.6 g/L; for cellobiose is 50 g/L [(4×46)/342]=26.9 g/L; and for xylose is 50 g/L [(10× 46)/(6×150)]=25.6 g/L. Fermentation efficiency was calculated by (50 g/L−residual sugar g/L)×100/50 g/L.

h (about 18 g/L ethanol), these strains produced only about 3 g/L with xylose at 96 h. Less than half the consumed xylose was converted to ethanol.

Example 3

Fermentation in DASGIP Fedbatch-Pro System

Fermentations were performed in a Fedbatch-pro fermentation system (DASGIP BioTools, LLC, Shrewsbury, Mass., USA) maintained at 30° C. with stirring (150 rpm) with oxygen in the headspace for aerobic conditions and headspace and reactor purged with nitrogen for anaerobic conditions. Liquid precultures were inoculated with colonies of yeast and incubated for 2 days at 30° C. with shaking at 100 rpm. The density of the preculture was adjusted to an absorbance equivalent to 4.0 at 660 nm, and 25 mL were added to 150 mL of medium in a 400-mL DASGIP culture vessel. Ethanol production was measured from YPX medium consisting of 10 g/L Yeast Extract, 20 g/L Bacto Peptone, and 20 g/L xylose (Thermo Fisher Scientific, Waltham, Mass., USA) and from mixed YPD, consisting of 10 g/L Yeast Extract, 20 g/L Bacto Peptone, and 20 g/L glucose, plus YPX.

Ethanol Production and Substrate Use by Mutagenized Strains in Fermentor

Figure 1B:
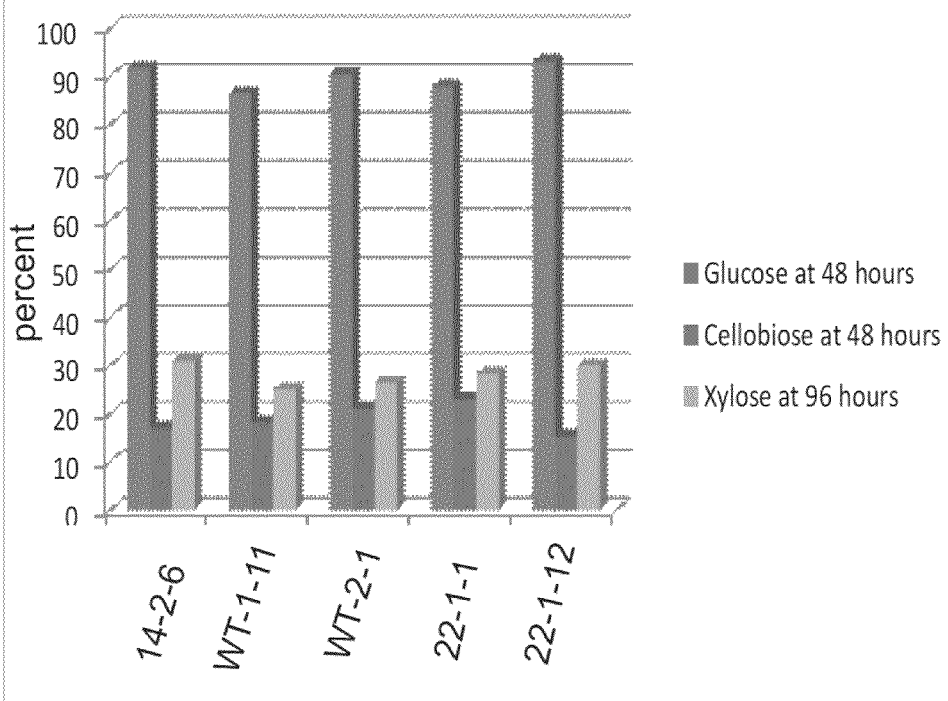
FIG. 1B is a graph depicting fermentation efficiency results for mutagenized strains using glucose, cellobiose, or xylose as substrate in 250-mL flasks.

Ethanol production under strictly anaerobic conditions (media and reactor headspace purged with nitrogen prior to inoculation) by mutagenized strains WT-1-11, 22-1-12, and 14-2-6 compared to Saccharomyces cerevisiae NRRL Y-2034 with glucose plus xylose medium over a period of about 500 h is displayed in FIG. 1A. It was not possible to evaluate Scheffersomyces stipitis NRRL Y-7124 because it does not grow under strictly anaerobic conditions. Saccharomyces cerevisiae NRRL Y-2034 reached maximum ethanol production of about 9.5 g/L within 12 h with no further increase

TABLE 2

| | Strain | Ethanol (g/L) | Ethanol yield (% theoretical) | Ethanol productivity (g/L/h) | Residual sugar (g/L) | Fermentation efficiency (%) |
|---|---|---|---|---|---|---|
| Glucose fermentation results at 48 hours | 14-2-6 (NRRL Y-50472) | 17.88 | 70.12 | 0.373 | 4.11 | 91.8 |
| | WT-1-11 | 16.97 | 66.55 | 0.354 | 6.68 | 86.6 |
| | WT-2-1 | 17.21 | 67.49 | 0.359 | 4.81 | 90.4 |
| | 22-1 | 16.51 | 64.75 | 0.344 | 6.07 | 87.9 |
| | 22-1-12 (NRRL Y-50473) | 18.39 | 72.12 | 0.383 | 3.39 | 93.2 |
| Cellobiose fermentation results at 48 hours | 14-2-6 (NRRL Y-50472) | 0.71 | 2.78 | 0.015 | 41.48 | 17.0 |
| | WT-1-11 | 0.70 | 2.75 | 0.015 | 40.91 | 18.2 |
| | WT-2-1 | 0.87 | 3.41 | 0.071 | 39.50 | 21.0 |
| | 22-1-1 | 0.75 | 2.94 | 0.061 | 38.44 | 23.1 |
| | 22-1-12 (NRRL Y-50473) | 0.61 | 2.39 | 0.05 | 42.34 | 15.3 |
| Xylose fermentation results at 96 hours | 14-2-6 (NRRL Y-50472) | 3.26 | 12.78 | 0.034 | 34.54 | 30.9 |
| | WT-1-11 | 1.92 | 7.53 | 0.020 | 37.47 | 25.1 |
| | WT-2-1 | 2.36 | 9.26 | 0.025 | 36.75 | 26.5 |
| | 22-1-1 | 2.94 | 11.53 | 0.031 | 35.83 | 28.3 |
| | 22-1-12 (NRRL Y-50473) | 2.99 | 11.73 | 0.031 | 34.98 | 30.0 |

When evaluated for growth on glucose, xylose, and cellobiose in 250-mL flasks, mutagenized strains 22-1-12 and 14-2-6 achieved the highest ethanol levels, productivities, and fermentation efficiencies on glucose, strains WT-2-1 and 22-1-1 performed slightly better than the other strains on cellobiose, and strains 14-2-6 and 22-1-12 performed best on xylose. However, compared to the results with glucose at 48

(some decrease in level is seen, possibly from evaporation) after glucose was depleted because this strain cannot utilize xylose. The mutagenized strains reached a level of ethanol production equal to the maximum level achieved by S. cerevisiae NRRL Y-2034 from 80 h (strain 22-1-12) to 180 h (strain WT-1-11). Ethanol production continued to increase for the mutagenized strains, which were capable of using xylo se as a substrate, reaching 13 g/L at 490 h (strains 22-1-12 and WT-1-11). The yield at that point was approximately 0.33 g ethanol/g glucose+xylose for these mutagenized *Scheffersomyces stipitis* strains in contrast to *Saccharomyces cerevisiae* NRRL Y-2034, which gave a maximum yield of approximately 0.24 g ethanol/g glucose+xylose.

Growth characteristics of mutagenized strains compared to wild-type (WT) strain, *Scheffersomyces stipitis* NRRL Y-7124, in liquid culture containing xylose and glucose under microaerophilic conditions (oxygen in headspace) in a DAS-GIP reactor are presented in Table 3. The mutagenized strains showed essentially the same pattern of cell growth, glucose consumption, xylose use, and ethanol production as the wild-type strain under the microaerophilic conditions needed by the wild-type strain, in addition to having acquired the ability to utilize xylose anaerobically for ethanol production.

TABLE 3

| Strain | Run Time H | Cell Density OD 600 | Volume mL | Glucose g/L | Glucose mmol | Xylose g/L | Xylose mmol | Ethanol g/L | Ethanol mmol |
|---|---|---|---|---|---|---|---|---|---|
| Y7124 | 0 | 1.00 | 210.0 | 18.54 | 21.61 | 19.23 | 26.89 | 0.24 | 1.10 |
|  | 8 | 1.20 | 209.0 | 16.71 | 19.39 | 19.22 | 26.75 | 1.12 | 5.06 |
|  | 16 | 5.32 | 208.0 | 14.48 | 16.71 | 18.56 | 25.71 | 1.81 | 8.16 |
|  | 24 | 6.60 | 207.0 | 13.19 | 15.16 | 18.63 | 25.69 | 2.39 | 10.75 |
|  | 32 | 6.94 | 206.0 | 12.75 | 14.58 | 19.55 | 26.83 | 2.96 | 13.24 |
|  | 43 | 7.92 | 205.0 | 11.29 | 12.85 | 18.79 | 25.66 | 3.28 | 14.60 |
|  | 67 | 8.74 | 204.0 | 9.44 | 10.69 | 19.13 | 25.99 | 4.22 | 18.68 |
|  | 108 | 9.36 | 203.0 | 7.14 | 8.05 | 19.17 | 25.93 | 5.18 | 22.85 |
|  | 138 | 10.18 | 202.0 | 5.38 | 6.03 | 18.62 | 25.05 | 5.82 | 25.54 |
|  | 207 | 10.80 | 201.0 | 1.70 | 1.90 | 18.71 | 25.05 | 7.71 | 33.63 |
|  | 378 | 11.24 | 200.0 | 0.00 | 0.00 | 15.81 | 21.06 | 9.33 | 40.49 |
|  | 500 | 9.96 | 199.0 | 0.00 | 0.00 | 13.76 | 18.24 | 10.08 | 43.55 |
| 14-2-6 | 0 | 1.00 | 210.0 | 18.88 | 22.00 | 19.55 | 27.34 | 0.24 | 1.11 |
| (NRRL Y- | 8 | 1.11 | 209.0 | 15.97 | 18.52 | 18.29 | 25.47 | 1.08 | 4.90 |
| 50472) | 16 | 5.76 | 208.0 | 14.55 | 16.80 | 18.74 | 25.97 | 1.93 | 8.74 |
|  | 24 | 7.26 | 207.0 | 12.46 | 14.32 | 18.00 | 24.82 | 2.48 | 11.14 |
|  | 32 | 7.55 | 206.0 | 12.21 | 13.96 | 19.36 | 26.57 | 3.15 | 14.08 |
|  | 43 | 8.12 | 205.0 | 10.77 | 12.26 | 18.74 | 25.59 | 3.51 | 15.63 |
|  | 67 | 9.02 | 204.0 | 8.79 | 9.95 | 18.48 | 25.11 | 4.21 | 18.66 |
|  | 108 | 9.52 | 203.0 | 6.72 | 7.58 | 18.83 | 25.45 | 5.27 | 23.24 |
|  | 138 | 9.86 | 202.0 | 5.38 | 6.03 | 18.96 | 25.51 | 6.01 | 26.34 |
|  | 207 | 9.62 | 201.0 | 2.10 | 2.34 | 18.94 | 25.36 | 7.60 | 33.16 |
|  | 378 | 10.50 | 200.0 | 0.00 | 0.00 | 16.55 | 22.04 | 9.18 | 39.86 |
|  | 500 | 9.98 | 199.0 | 0.00 | 0.00 | 14.96 | 19.83 | 9.72 | 42.00 |
| 22-1-1 | 0 | 1.00 | 210.0 | 18.60 | 21.68 | 19.25 | 26.92 | 0.31 | 1.39 |
|  | 8 | 1.31 | 209.0 | 16.07 | 18.64 | 18.86 | 26.25 | 1.35 | 6.11 |
|  | 16 | 6.08 | 208.0 | 14.42 | 16.65 | 19.22 | 26.63 | 2.21 | 9.96 |
|  | 24 | 7.56 | 207.0 | 12.59 | 14.46 | 18.64 | 25.70 | 2.74 | 12.29 |
|  | 32 | 8.75 | 206.0 | 11.87 | 13.57 | 19.10 | 26.21 | 3.25 | 14.52 |
|  | 43 | 9.26 | 205.0 | 10.80 | 12.28 | 18.87 | 25.76 | 3.62 | 16.10 |
|  | 67 | 9.46 | 204.0 | 8.47 | 9.59 | 17.97 | 24.41 | 4.21 | 18.65 |
|  | 108 | 9.86 | 203.0 | 6.62 | 7.46 | 19.06 | 25.77 | 5.52 | 24.31 |
|  | 138 | 10.62 | 202.0 | 5.12 | 5.74 | 18.79 | 25.27 | 6.11 | 26.78 |
|  | 207 | 9.94 | 201.0 | 1.79 | 2.00 | 18.59 | 24.89 | 7.66 | 33.44 |
|  | 378 | 13.06 | 200.0 | 0.00 | 0.00 | 16.78 | 22.35 | 8.80 | 38.22 |
|  | 500 | 11.14 | 199.0 | 0.00 | 0.00 | 16.45 | 21.81 | 9.00 | 38.90 |
| (NRRL Y- | 0 | 1.00 | 210.0 | 18.67 | 21.77 | 19.36 | 27.07 | 0.29 | 1.31 |
| 50473) | 8 | 1.13 | 209.0 | 15.88 | 18.43 | 18.44 | 25.66 | 1.02 | 4.63 |
| 22-1-12 | 16 | 5.55 | 208.0 | 14.37 | 16.59 | 18.79 | 26.04 | 2.02 | 9.13 |
|  | 24 | 7.08 | 207.0 | 12.59 | 14.47 | 18.34 | 25.28 | 2.57 | 11.54 |
|  | 32 | 7.24 | 206.0 | 12.00 | 13.72 | 18.95 | 26.00 | 3.11 | 13.89 |
|  | 43 | 7.52 | 205.0 | 10.88 | 12.38 | 18.60 | 25.40 | 3.46 | 15.42 |
|  | 67 | 8.44 | 204.0 | 8.88 | 10.05 | 18.40 | 25.00 | 4.27 | 18.89 |
|  | 108 | 8.16 | 203.0 | 6.99 | 7.88 | 18.94 | 25.61 | 5.30 | 23.36 |
|  | 138 | 8.92 | 202.0 | 5.45 | 6.11 | 18.56 | 24.97 | 5.96 | 26.15 |
|  | 207 | 8.54 | 201.0 | 2.26 | 2.52 | 18.50 | 24.77 | 7.58 | 33.07 |
|  | 378 | 11.56 | 200.0 | 0.00 | 0.00 | 16.97 | 22.60 | 8.97 | 38.94 |
|  | 500 | 9.78 | 199.0 | 0.00 | 0.00 | 16.64 | 22.05 | 9.07 | 39.20 |

When mutagenized *Scheffersomyces stipitis* strains were compared to wild-type *S. stipitis* NRRL Y-7124, in liquid culture containing xylose and glucose under microaerophilic conditions (oxygen in reactor headspace), the mutagenized strains produced 9.0 to 9.7 g/L ethanol, which was close to that of the wild-type strain under the same conditions. The yields for the mutagenized *S. stipitis* strains were 0.23 to 0.24 g ethanol/g glucose+xylose, compared with 0.27 g ethanol/g glucose+xylose for the wild-type *S. stipitis* strain.

Example 4

Ethanol Yield Under Facultative Conditions

Figure 6:
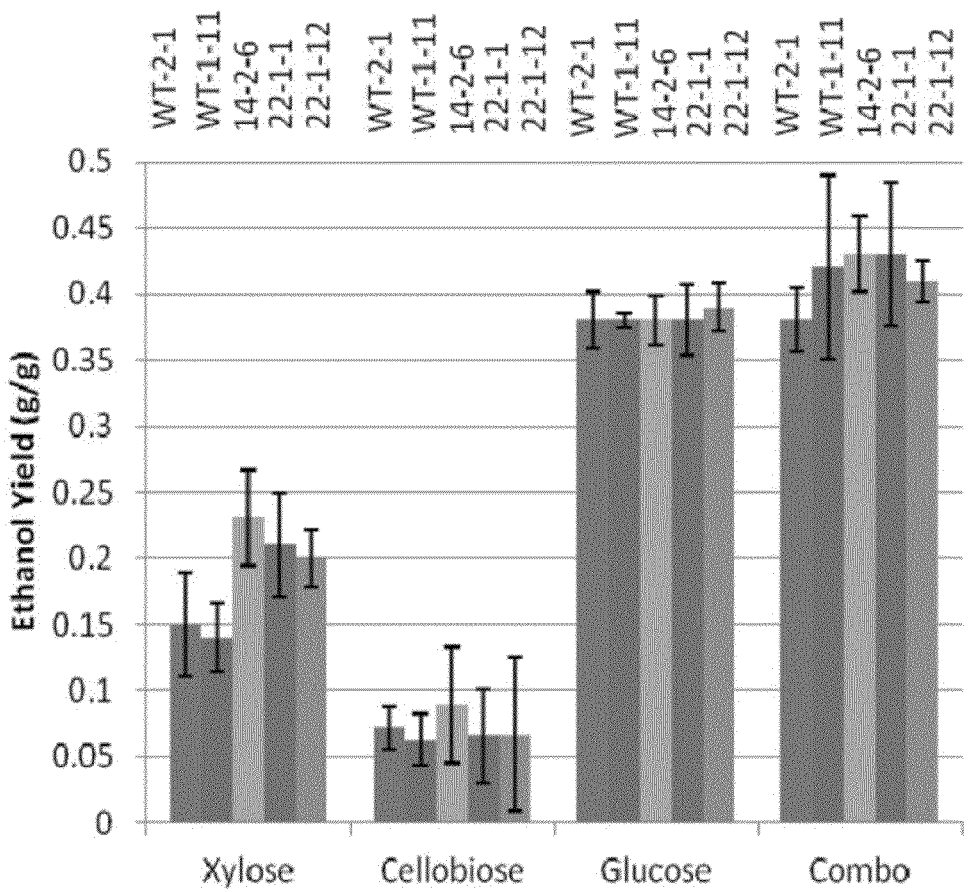
FIG. 6 is a graph depicting ethanol yield of mutagenized *Sheffersomyces* (*Pichia*) *stipitis* strains WT-2-1, WT-1-11, 14-2-6 (NRRL Y-50472), 22-1-1, and 22-1-12 (NRRL Y-50473) under facultative conditions.

Ethanol yields of mutagenized strains WT-2-1, WT-1-11, 14-2-6, 22-1-1, and 22-1-12 were evaluated under facultative conditions with sugar sources of glucose, xylsoe, cellobiose, and a combination of the three sugars and is displayed in FIG. 6. Media were prepared by mixing 50 g/L of each individual sugar with 5 g/L of yeast extract. In the combination medium comprised of a mixture of 16.7 g of each sugar with 5 g/L of yeast extract. The pH of the various media was ~6. The optimal pH for *S. stipitis* fermentation of xylose is reportedly 5.5 to 6. For facultative trials, media (100 mL) were dispensed into 250-mL Erlenmeyer flasks equipped with a rubber stopper and needle/filter for gas exchange. Media were autoclaved prior to use.

Inoculum for each trial was prepared by subculturing into 100 mL of an appropriate medium in a 250-mL Erlenmeyer flask. For trials with glucose, cellobiose, and the combination medium, an inoculum medium containing glucose was used while for trials with xylose, the inoculum medium containing xylose. Inoculum cultures were incubated at 35° C. in a rotary shaker (200 rev/min) for 24 h prior to use. An inoculum volume of 1% v/v was used in all trials. Three trials were performed for each sugar or sugar combination. All flasks or serum bottles were placed into a rotary shaker (200 rev/min) set at 35° C. for 96 h. Samples (4 mL) were taken at 0, 3, 6, 9, 12, 24, 36, 48, 72, and 96 h. One milliliter was used for viable cell counts, whereas the remaining 3 mL was filtered through a 0.2-micron filter and placed in high-performance liquid chromatography (HPLC) vials that were frozen (−20° C.) until analysis.

Viable cells counts were performed using a hemocytometer. One milliliter of sample was diluted with 9 mL of distilled water and a drop of methylene blue. Samples were analyzed for glucose, xylose, cellobiose, xylitol, lactic acid, acetic acid, and ethanol using a Waters (Milford, Mass.) HPLC system with a refractive index detector. A Bio-Rad (Hercules, Calif.) Aminex HPX-87H column was used, and the mobile phase was 0.005 M $H_2SO_4$ at a flow rate of 0.6 mL/min.

Ethanol yield was calculated as the amount of ethanol produced per gram of sugar consumed (FIG. 6) to differentiate the relative efficiency of ethanol production by the listed strains. Although there was no difference between strains in the cellobiose, glucose, and sugar combination trials, strains 22-2-12, 22-1-1, and 14-2-6 outperformed strain WT-1-11 on xylose. Trends between the sugars showed an average yield of 0.38 g/g on glucose and 0.38 to 0.43 g/g on the sugar combination.

Example 5

Ethanol Yield Under Anaerobic Conditions

Figure 7:
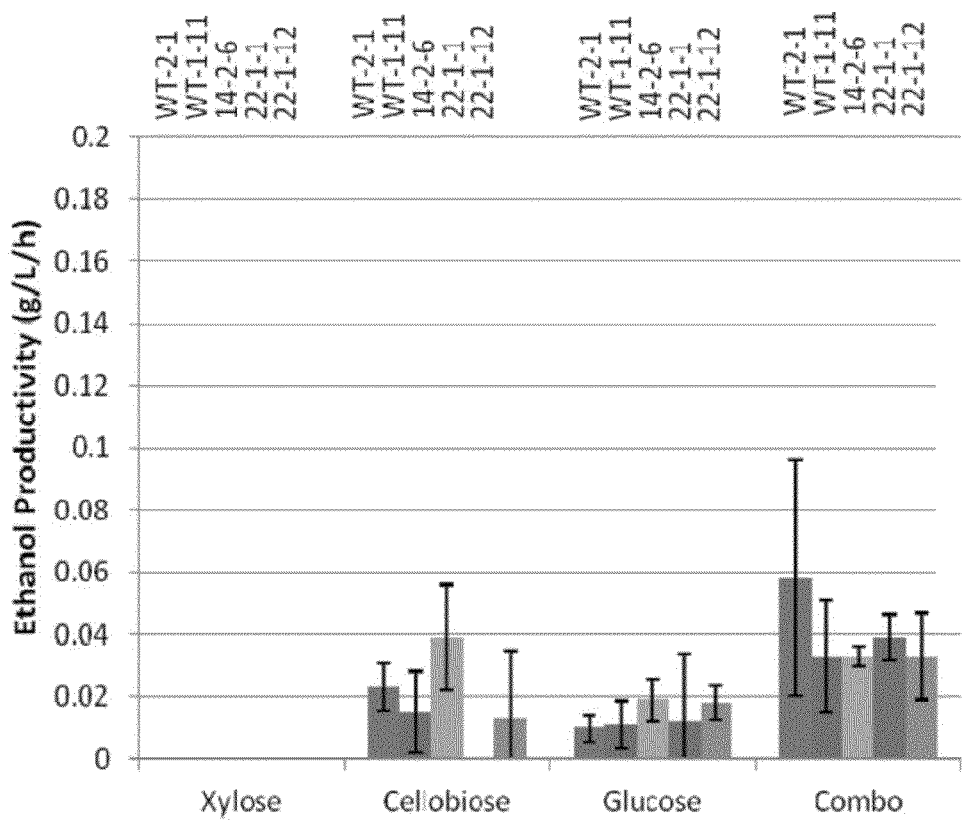
FIG. 7 is a graph depicting ethanol yield of mutagenized *Sheffersomyces* (*Pichia*) *stipitis* strains WT-2-1, WT-1-11, 14-2-6 (NRRL Y-50472), 22-1-1, and 22-1-12 (NRRL Y-50473) under anaerobic conditions.

Ethanol yields of mutagenized strains WT-2-1, WT-1-11, 14-2-6, 22-1-1, and 22-1-12 were evaluated under facultative conditions with sugar sources of glucose, xylsoe, cellobiose, and a combination of the three sugars and is displayed in FIG. 7. Ethanol yield trials for the strains were conducted under condition as disclose in Example 4 with the difference being media were dispensed into 75-mL serum bottles, purged with nitrogen to remove oxygen, and sealed for anaerobic conditions.

Other than a slightly higher ethanol yield with cellobiose, ethanol yields for the other sugars were much lower anaerobically (FIG. 7) than under facultative conditions.

Example 6

DNA Fingerprinting

Variable nucleotide tandem repeat (VNTR) PCR analysis was performed to detect differences in genomic DNA sequences between strains using as the PCR primer the 28-base pair (bp) repeating unit of the highly polymorphic VNTR sequences present in the 3' flanking region of the HRAS gene: 5'AGGGGACGCCACACTCGCCCT-TCTCTCC 3'. (SEQ. ID. No.: 1) The sequence is related to fungal primers but was found to produce fewer background bands when the PCR products were run on an agarose gel.

Genomic DNA was isolated from cells in a 2-day culture (1 g wet weight). Cells were frozen in liquid nitrogen, broken up with a mortar and pestle, scraped into a 15-mL conical tube, and DNA isolated using the Qiagen DNeasy Plant Genomic kit (Qiagen, Inc., Valencia, Calif., USA) according to manufacturer's directions.

PCR was carried out in a PTC-225 Tetrad Thermal Cycler (Bio-Rad Laboratories, Hercules, Calif., USA) using the following conditions: hold at 96° C. for 5 minutes, cycle at 96° C. for 1 minute, 65° C. for 1 minute, 72° C. for 1 minute, repeated for 30 times, followed by 72° C. for 7 minutes and a 4° C. hold. The procedure amplified the genomic sequence between two VNTR sequences to determine alterations in the microsatellite or minisatellite regions in the genome caused by UV-C mutagenization. The amplified DNA was analyzed by gel electrophoresis on 1% (w/v) agarose gels stained with ethidium bromide.

Differences in Strains Detected Using VNTR PCR from Genomic DNA

Differences in genomic DNA sequences between strains were detected using variable nucleotide tandem repeat (VNTR) PCR analysis. A high degree of polymorphism is often present with respect to the number of tandemly repeated units of a nucleotide sequence at a particular locus on the genome of an organism. These differences result in differences in PCR products amplified using the VNTR sequence as PCR primer and can be used to distinguish differences in the genome. The DNA fingerprints for mutagenized *S. stipitis* strains WT-1-11, WT-2-1, 14-2-6, 22-1-1, and 22-1-12 compared to the wild-type (WT) strains, *S. stipitis* NRRL Y-7124 and *Saccharomyces cerevisiae* Y-2043, are presented in FIG. 2.

Figure 2:
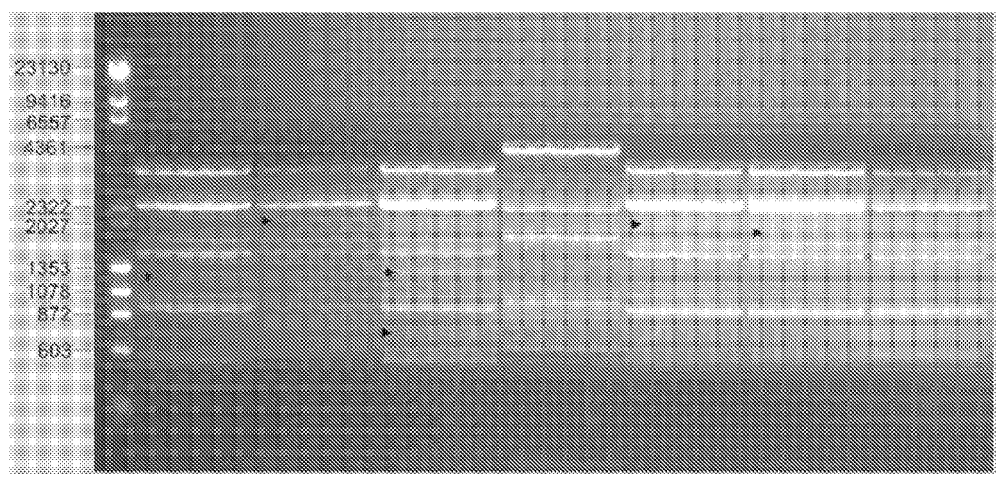
FIG. 2 is a photograph of an agarose gel showing variable nucleotide tandem repeat (VNTR) analysis of the changes to the genomic DNA of mutagenized *Sheffersomyces* (*Pichia*) *stipitis* strains WT-1-11, WT-2-1, 14-2-6 (NRRL Y-50472), 22-1-1, and 22-1-12 (NRRL Y-50473) compared to the wild-type (WT) strain, *S. stipitis* NRRL Y-7124. *Saccharomyces cerevisiae* NRRL Y-2034 is provided for comparison. Resulting PCR products using the fungal VNTR primer generated fragments that are indicative of changes to the genomes of the mutagenized strains and analyzed on a 1% (w/v) agarose gel. Bionexus DNA by markers are identified by length on the left side of the figure. Bands present in mutagenized strains but not present in wild-type *Sheffersomyces* (*Pichia*) *stipitis* NRRL Y-7124 are indicated by arrows. Gel was run at 80 volts on a Bio-Rad Power Pac 3000 and a high-resolution digital image file was generated with an AlphaImager™ 3400 using a trans-UV light.

New banding patterns generating a distinct fingerprint for each of the mutagenized strains that grew anaerobically on xylose are shown on the agarose gel (FIG. 2). The arrows point out bands that are present in the fingerprints of the 5 mutagenized strains but not in the fingerprint of *Scheffersomyces stipitis* NRRL Y-7124 wild-type strain. Strains WT-2-1 and 14-2-6 both have new bands at approximately 1200 basepairs that are not present in the other mutagenized strains; however, strain 14-2-6 has a new band at approximately 700 bp that does not appear in strain WT-2-1 or any of the other strains. Strains WT-1-11 and 22-1-12 both have one new band at 2027 bp that is not seen in wild-type strain Y-7124; however WT-1-11 does not have the intense band observed in strain 22-1-12 at approximately 900 base pairs.

To the extent that the term "includes" or "including" is employed in the detailed description or the claims, it is intended to be inclusive in a manner similar to the term "comprising" as that term is interpreted when employed as a transitional word in a claim. Furthermore, to the extent that the term "or" is employed in the detailed description or claims (e.g., A or B) it is intended to mean "A or B or both". When the applicants intend to indicate "only A or B but not both" then the term "only A or B but not both" will be employed. Thus, use of the term "or" herein is the inclusive, and not the exclusive use. See, Bryan A. Garner, A Dictionary of Modern Legal Usage 624 (2d. Ed. 1995). Also, to the extent that the terms "in" or "into" are used in the specification or the claims, it is intended to additionally mean "on" or "onto." Furthermore, to the extent the term "connect" is used in the specification or claims, it is intended to mean not only "directly connected to," but also "indirectly connected to" such as connected through another component or components.

While the invention has been described with reference to details of the illustrated embodiment, these details are not intended to limit the scope of the invention as defined in the appended claims.

The embodiment of the invention in which exclusive property or privilege is claimed is defined as follows:

1. An isolated *Scheffersomyces stipitis* having been deposited with the United States Department of Agriculture, Agricultural Research Patent Culture Collection as Accession Deposit Number NRRL Y-50472.

2. A method of producing ethanol comprising culturing yeast strain NRRL Y-50472 under suitable conditions for a period of time sufficient to allow fermentation of at least a portion of feedstock to ethanol.

3. The method of claim 2 in which the feedstock includes cellobiose and glucose and the yeast strain NRRL Y-50472 is cultured under anaerobic conditions.

4. The method of claim 2 wherein the yeast strain NRRL Y-50472 is cultured under microaerophilic conditions to ferment cellobiose.

5. The method of claim 2 wherein the yeast strain NRRL Y-50472 is cultured under anaerobic or aerobic conditions to ferment cellobiose.

6. The method of claim 2 wherein the yeast strain NRRL Y-50472 is cultured under aerobic conditions to ferment a combination of xylose, cellobiose and glucose.

* * * * *

```
                              SEQUENCE LISTING

<160> NUMBER OF SEQ ID NOS: 1

<210> SEQ ID NO 1
<211> LENGTH: 28
<212> TYPE: DNA
<213> ORGANISM: Artificial Sequence
<220> FEATURE:
<223> OTHER INFORMATION: Primer

<400> SEQUENCE: 1
aggggacgcc acactcgccc ttctctcc                                          28
```